United States Patent
Kriz et al.

(10) Patent No.: US 7,078,234 B2
(45) Date of Patent: Jul. 18, 2006

(54) MAIZE EMBRYO-SPECIFIC PROMOTER COMPOSITIONS AND METHODS FOR USE THEREOF

(75) Inventors: Alan L. Kriz, Gales Ferry, CT (US); Dale A. Voyles, Pawcatuck, CT (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 10/732,721

(22) Filed: Dec. 10, 2003

(65) Prior Publication Data

US 2004/0163144 A1     Aug. 19, 2004

Related U.S. Application Data

(60) Provisional application No. 60/434,242, filed on Dec. 17, 2002.

(51) Int. Cl.
| | |
|---|---|
| C12N 15/82 | (2006.01) |
| C12N 15/90 | (2006.01) |
| C07H 21/04 | (2006.01) |
| A01H 5/00 | (2006.01) |
| A01H 5/10 | (2006.01) |

(52) U.S. Cl. ............... 435/468; 435/320.1; 800/287; 536/24.1

(58) Field of Classification Search ............. 435/320.1, 435/419, 468; 536/23.6, 24.1; 800/295, 800/298

See application file for complete search history.

(56) References Cited

OTHER PUBLICATIONS

Kim et al. 1994. Plant Mol Biol. vol. 24. p. 105-117.*
Williams and Tsang, Nucleotide sequence of an abscisic acid-responsive, embryo-specific maize gene, Plant Physiology, 1992, 100:1067-1068.
Williams and Tsang, Analysis of multiple classes of abscisic acid-responsive genes during embryogenesis in Zea mays, Developmental Genetics, 1994, 15:415-424.

* cited by examiner

*Primary Examiner*—Ashwin Mehta
(74) *Attorney, Agent, or Firm*—Maria Margarita D. Unson; Thomas F. Kelley (57) ABSTRACT

This invention provides an embryo specific promoter, e.g. derived from the 5' regulatory region of an emb5 gene. Compositions comprising this promoter include DNA constructs useful for plant transformation and plants transformed with such DNA constructs. Further provided are methods for the expression of transgenes in plants using the embryo specific promoter sequences. The methods of the invention include the direct creation of transgenic plants with the emb5 promoter by genetic transformation, as well as by plant breeding methods. The sequences of the invention represent a valuable new tool for the creation of transgenic plants, preferably having one or more added beneficial characteristics.

18 Claims, 4 Drawing Sheets

FIG. 1: Sequence of the 1658 bp embryo specific *emb5* promoter (SEQ ID NO:1).

```
gaattcacggctcacaataccagtcatcatcacgtgtgataaatttatagttagattacttcttgtaatcatttcagagagatgaaaaaaa
atcgaagaaagcaaatatttaaatgatgcaatatacaaattaattacacaattatgtaagattacatgtttagttcatagaa
atcaaattctagagtcataataatgcctaaattaaaattctattctatttttcttaagaaaaaacagccattaagggaccattaga
atgcgcgtctccatttttatatatagagatatgagttgtgttgctcactagccacctcgcatgcgtgtctttattacatgaaaa
aatgagccgctgcttttgcattaagggtctagagatgtacgagtgcaacgcttcgtattcactgacgagtaattttttaatgcacgg
aggcgctttgtattcctcagcagctctgcgccgtcgttcgtgtacgtgcagtgcgagtgacgaggcagcagcagctcacgtgcccacgt
gcctggctgcctgccaccgtgatgcaaggcttgctgttgctgcgcagtgtggcgagcgacgaggttgaagctacgcggtg
gctgcttgcctgcgcgctagcacggcgacgacgtcgacgctgatgctagcgttgctacttttgttttctcctgtctgcatg
atgcagtaaataaacgtgtatctcatgtgattgatcgacgtgtcggcgatttcaaatcagtaacaatcacatgtcatcccat
cgacttcgtgtgcgcgataaatctgctagggattgtgctttcatgtatgtgcttgaatagagagaagaatatatattaaata
tgagttcaacatcttcttaatacctttgctctgatcctccttagtagagcacgttaagaaccccttgttaccgagtg
tagtccaaggctgctttaactgaataatagtagaacacaagaggagacaagaagttgagagaggaactgattcttgtactatatggtgc
tgctctccaaaggttacatgatgatgggatctctctctatttataagacaaaacataggttcaggcatatggccacataggccttcct
ggcccaagaaaggtttcttaacactaccatcttcaggcgcggtgtcgttcaactcttccctccgccttccagagcggataa
ataccgggtctacggtgcacgcacgtggccgaggggcatgtgccgaggggccccacacgcgtgcgccgcccgagggcgccatgcctgcgac
acgcacgtacgtgtcgccccgcgagcctcctcgcacgcgtcgcgccgaggacttgcaattcgtccg
cgtcggtgcacacgtccctggtccggttgccgggtccgtggccctggcctgccgcgcgacgtgccgctgctcccaccgacggctat
aaaaaggcgcgccacctgatcctccacaagcaacaagcagcagcagcaacacctaaactaaagaacagtag
tagtccctgtgtacgtctctagcaacgatccgccgcacgatccgcgccgagctcgccgccagttgctcgttagttttgggacggcg
```

FIG. 2: Map of vector pDPG829.

FIG. 3: Map of vector pDPG830.

FIG. 4: Map of vector pMON67914

MAIZE EMBRYO-SPECIFIC PROMOTER COMPOSITIONS AND METHODS FOR USE THEREOF

PRIORITY CLAIM AND INCORPORATION OF SEQUENCE LISTING

This application claims benefit of priority to the following application: U.S. Provisional Application Ser. No. 60/434,242, entitled "Maize Embryo-Specific Promoter Compositions and Methods for use Thereof" and filed 18 Dec. 2002. This application further incorporates by reference in its entirety herein the sequence listing contained in the file named "Maize Embryo-Specific Promoter Compositions and Methods for use Thereof" which is 3,000 bytes (measured in MS-Windows) and was created on Dec. 17, 2002 and is located on a diskette filed with application Ser. No. 60/434,242.

BACKGROUND OF THE INVENTION

The present invention relates to the field of agricultural biotechnology. Disclosed herein are DNA constructs with an embryo-specific promoter, transgenic plants comprising such DNA constructs with an embryo-specific promoter, and methods of making and using such DNA constructs and transgenic plants.

In brief, a fertile corn plant contains both male and female reproductive tissues, commonly known as the tassel and the ear, respectively. The tassel tissues form the haploid pollen grains with two nuclei in each grain, which, when shed at anthesis, contact the silks of a female ear. The ear may be on the same plant as that which shed the pollen, or on a different plant. The pollen cell develops a structure known as a pollen tube, which extends down through an individual female silk to the ovule. The two male nuclei travel through this tube to reach the haploid female egg at the base of the silk. One of the male nuclei fuses with and fertilizes the female haploid egg nuclei to form the zygote, which is diploid in chromosome number and will become the embryo within the kernel. The remaining male nucleus fuses with and fertilizes a second female nucleus to form the primary endosperm nucleus, which is triploid in number and will become the endosperm of the kernel, or seed, of the corn plant. Non-fertilized ovules do not produce kernels and the unfertilized tissues eventually degenerate.

The kernel consists of a number of parts, some derived from maternal tissue and others from the fertilization process. Maternally, the kernel inherits a number of tissues, including a protective, surrounding pericarp and a pedicel. The pedicel is a short stalk-like tissue which attaches the kernel to the cob and provides nutrient transfer from maternal tissue into the kernel. The kernel contains tissues resulting from the fertilization activities, including the new embryo as well as the endosperm. The embryo is the miniature progenitor of the next generation, containing cells for root and shoot growth of a new, young corn plant. It is also one tissue in which oils and proteins are stored in the kernel. The endosperm functions more as a nutritive tissue and provides the energy in the form of stored starch, proteins and oil, needed for the germination and initial growth of the embryo.

Considering the complex regulation that occurs during embryo and kernel development in higher plants, and considering that it is commonly grain that is a primary source of nutrition for animals and humans, key tools needed to improve such a nutritional source include genetic promoters that can drive the expression of nutrition enhancing genes. Unfortunately, relatively few promoters specifically directing this aspect of physiology have been identified. Accordingly, there is a need in the art for novel promoter sequences which are involved in kernel development, and more particularly, embryo development.

SUMMARY OF THE INVENTION

This invention provides embryo-specific, developmentally regulated promoters that may be operably linked to a number of genes to affect, for example, embryo development, kernel development, germination, grain yield, grain quality, pest resistance, stress resistance, fertility, decreased kernel abortion and the like. In particular, this invention provides embryo-specific promoters for use in plants which are derived from the 5' regulatory region of an emb5 gene. In one embodiment of the invention, the promoter is derived from the 5' regulatory region of a maize emb5 gene and has a nucleotide sequence identical to part or all of SEQ ID NO:1.

This invention provides DNA constructs with an embryo-specific promoter which is useful for expressing exogenous DNA in maize embryos during development, methods for providing plants which express a gene of interest in embryos during development, and transgenic plants having such DNA constructs. One aspect of the invention provides a DNA construct comprising a promoter operably linked to an exogenous DNA, where the promoter is derived from part or all of the 5' regulatory region of a maize emb5 gene and exhibits promoter activity. Another aspect of the invention provides DNA constructs where the promoter comprises at least about 100 contiguous nucleotides which are identical to a nucleic acid molecule having the sequence of SEQ ID NO:1. In another embodiment, the invention provides DNA constructs where the promoter comprises at least about 125 nucleotides, about 500 nucleotides or about 1000 nucleotides or more which are identical to a nucleic acid molecule having the sequence of SEQ ID NO:1. Still other aspects provide a DNA construct where the promoter comprises a segment of nucleic acid sequence which is at least 85% identical with a functional part of SEQ ID NO:1, e.g., preferably at least about a 125 contiguous nucleotide segment of SEQ ID NO:1, or a larger fragment of the natural promoter regulatory region, e.g., at least about a 250, or 500, or 1000, or even 1500 contiguous nucleotide segment. Other aspects of the invention provide a suitable DNA construct where the promoter comprises the CAAT and TATA box elements naturally associated with the natural promoter. Yet another aspect of the invention provides a suitable DNA construct where the embryo-specific promoter is operably linked to an exogenous DNA which encodes a molecule imparting, for example, enhanced embryo development or kernel agronomic traits. Another aspect of the invention provides a DNA construct in which the embryo-specific promoter drives a gene suppression DNA element, e.g. to suppress an amino acid catabolizing enzyme.

Another aspect of this invention provides a method for preparing a plant which expresses a gene of interest in maize kernel embryos during development comprising introducing into the genome of the plant a DNA construct comprising an embryo-specific promoter operably linked to exogenous DNA desired to be expressed in maize kernel embryos during development.

A further aspect of this invention provides transgenic plants with an embryo-specific promoter of this invention operably linked to exogenous DNA, e.g., a gene of interest.

More particularly such a transgenic plant has in its genome a DNA construct according to this invention, e.g., a DNA construct comprising a promoter operably linked to exogenous DNA where the promoter is derived from the 5' regulatory region of a maize emb5 gene.

The transgenic plant may be a monocot or a dicot. A preferred monocot transgenic plant may be selected from the group consisting of wheat, oat, barley, maize, rye, rice, turfgrass, sorghum, millet and sugarcane, more preferably maize, wheat and rice. A preferred dicot transgenic plant may be selected from the group consisting of canola, cotton, safflower, soybean, sugarbeet, sunflower, more preferably soybean, canola and cotton.

The invention also provides for transgenic plants comprising an embryo-specific promoter of this invention in combination with an enhancer, for example, an intron. In one embodiment, the enhancer intron is a rice actin 1 intron 1 (U.S. Pat. No. 5,641,876, incorporated herein by reference in its entirety) or a rice actin 2 intron 1 (U.S. Pat. No. 6,429,357, incorporated herein by reference in its entirety). The promoter element may further comprise a 3' untranslated region (3' UTR), such as a nos 3' UTR or Tr7 3' UTR.

Potentially any exogenous DNA can be operably linked to the embryo-specific promoter, including, for example, a selected sequence which encodes a molecule imparting insect resistance, bacterial disease resistance, fungal disease resistance, viral disease resistance, nematode disease resistance, herbicide resistance, enhanced grain composition or quality, nutrient transporter functions, enhanced nutrient utilization, enhanced environmental stress tolerance, reduced mycotoxin contamination, female sterility, a selectable marker phenotype, a screenable marker phenotype, a negative selectable marker phenotype, altered plant agronomic characteristics, or a combination thereof. In preferred aspects of this invention, the embryo-specific promoter is operably linked to heterologous DNA which encodes a molecule imparting enhanced kernel development, embryo development, general production or protection of next-generation tissues, or grain agronomic characteristics.

The selected exogenous DNA may further comprise DNA from a cloning vector, such as plasmid DNA, or alternatively, may be introduced as an expression cassette isolated from such vector DNA. The selected exogenous DNA may also comprise a sequence encoding a signal peptide. Examples of signal peptides include a peroxisomal targeting peptide or a chloroplast transit peptide. Examples of a chloroplast transit peptide include the group consisting of chlorophyll a/b binding protein transit peptide, small subunit of ribulose bisphosphate carboxylase transit peptide, EPSPS transit peptide and dihydrodipocolinic acid synthase transit peptide.

A transgenic plant prepared in accordance with the invention may be of any generation, including a fertile $R_0$ transgenic plant as well as progeny plants of any generation, and inbred or hybrid progeny plants thereof which contain the exogenous DNA. Also included within the invention are seeds of any such plants.

In still yet another aspect, the invention provides a method of plant breeding comprising the steps of: (i) obtaining a transgenic plant comprising an embryo specific promoter of this invention and (ii) crossing the transgenic plant with itself or a second plant. The transgenic plant may be of potentially any species, including monocotyledonous or dicotyledonous plants.

DETAILED DESCRIPTION OF THE INVENTION

1. Definitions

As used herein "coding sequence" means a DNA sequence which is a template for the production of an RNA molecule. The RNA may be an mRNA, which encodes a protein product, or a tRNA, rRNA, snRNA, antisense RNA, or other RNA molecule, such as a hairpin forming RNA molecule useful for gene suppression.

As used herein "exogenous DNA" refers to DNA which is not normally found next to the adjacent native DNA, i.e., a sequence not normally found in the host genome in an identical context. The DNA itself may be native to the host genome or may comprise the native sequence altered by the addition or deletion of one or more different regulatory elements or other sequences. The exogenous DNA may encode a protein or non-protein product. Likewise, "exogenous sequence" is a sequence of DNA not normally found in the host genome in an identical context. A transformation construct comprising a gene of interest, which originates or is produced outside of an organism, is an example of an exogenous DNA.

As used herein "expression" refers to the combination of intracellular processes, including transcription and translation, undergone by a DNA molecule, such as a structural gene to produce a polypeptide, or a non-structural gene to produce an RNA molecule.

As used herein "gene" means a DNA sequence from which an RNA molecule is transcribed. The RNA may be an mRNA which encodes a protein product, an RNA which functions as an anti-sense molecule, or a structural RNA molecule such as a tRNA, rRNA or snRNA, or other RNA.

As used herein "heterologous" DNA is any DNA sequence which is not naturally found next to the adjacent DNA. Heterologous DNA is often found in a DNA construct used for transformation. An emb5 promoter operably linked to a reporter gene is an example of a heterologous DNA as the emb5 promoter is naturally and normally associated with an emb5 gene.

As used herein "progeny" means any subsequent generation, including the seeds and plants therefrom, which is derived from a particular parental plant or set of parental plants; the resultant progeny line may be inbred or hybrid. Progeny of a transgenic plant of this invention can be, for example, self-crossed, crossed to a transgenic plant, crossed to a non-transgenic plant, and/or back crossed.

As used herein, "promoter" means a region of DNA sequence that is essential for the initiation of transcription of DNA, resulting in generation of an RNA that is complimentary to the transcribed DNA; this region may also be referred to as a "5' regulatory region." Promoters are located upstream of the coding sequence to be transcribed and have regions that act as binding sites for RNA polymerase and have regions that work with other factors to promote RNA transcription. More specifically, basal promoters in plants comprise canonical regions associated with the initiation of transcription, such as CAAT and TATA boxes. The TATA box element is usually located approximately 20 to 35 nucleotides upstream of the site of initiation of transcription. The CAAT box element is usually located approximately 40 to 200 nucleotides upstream of the start site of transcription. The location of these basal promoter elements result in the synthesis of an RNA transcript comprising nucleotides upstream of the translational ATG start site. The region of RNA upstream of the ATG is commonly referred to as a 5' untranslated region or 5' UTR. It is possible to use standard molecular biology techniques to make combinations of basal promoters, that is regions comprising sequences from the CAAT box to the translational start site, with other upstream promoter elements to enhance or otherwise alter promoter activity or specificity.

As used herein "promoter activity" characterizes a DNA sequence which initiates transcription of RNA from adjacent downstream DNA.

As used herein an "Ro transgenic plant" is a plant which has been directly transformed with a selected exogenous DNA or has been regenerated from a cell or cell cluster which has been transformed with a selected exogenous DNA.

As used herein "regeneration" means the process of growing a plant from a plant cell (e.g., plant protoplast, callus or explant).

As used herein "transformation construct" means a DNA molecule which is designed for introduction into a host genome by genetic transformation. Preferred transformation constructs comprise all of the genetic elements necessary to direct the expression of one or more exogenous sequences. Transformation constructs prepared in accordance with the instant invention include a promoter derived from a maize emb5 promoter. In particular embodiments of the instant invention, it may be desirable to introduce a transformation construct into a host cell in the form of an exogenous DNA construct.

As used herein "transgene" means a segment of exogenous DNA which has been incorporated into a host genome or is capable of autonomous replication in a host cell and is capable of causing the expression of one or more cellular products. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the exogenous DNA segment.

As used herein "transgenic plant" means a plant or progeny plant of any subsequent generation derived therefrom, wherein the DNA of the plant or progeny thereof contains an introduced exogenous DNA segment not originally present in a non-transgenic plant of the same strain. The transgenic plant may additionally contain sequences which are native to the plant being transformed, but wherein the exogenous gene has been altered in order to alter the level or pattern of expression of the gene.

As used herein a "stably" transformed plant is a plant in which the exogenous DNA is heritable. The exogenous DNA may be heritable as a fragment of DNA maintained in the plant cell and not inserted into the host genome. Preferably, the stably transformed plant comprises the exogenous DNA inserted into the chromosomal DNA in the nucleus, mitochondria or chloroplast, most preferably in the nuclear chromosomal DNA.

2. Embryo Specific Promoters

The current invention provides novel methods and compositions for the efficient expression of transgenes in plants, especially in the developing embryo. In particular, the current invention provides a promoter of a *Zea mays* late embryogenesis-abundant, embryo specific gene, emb5. The emb5 promoter described herein represents a developmentally regulated promoter from which expression increases from mid- to late-embryogenesis and then decreases in expression level as the embryo and kernel fully mature.

EMB5 is a late embryogenesis-abundant protein and the emb5 gene is abscisic-acid responsive and expressed in maize embryos. Williams and Tsang (*Dev. Genetics*, 15:415–424, 1994) reported that emb5 transcripts are first detected during mid-embryogenesis (approximately 21 days after pollination (DAP)) and accumulate to peak levels by late embryogenesis (about 27 DAP). RNA levels gradually decrease to very low levels as the seed matures to approximately 48 DAP. Emb5 transcripts show greatly reduced levels in kernels following imbibition and are not found in seedlings.

Expression specific promoters of this invention may be useful in minimizing yield drag and other potential adverse physiological effects on maize growth and development that might be encountered by high-level, non-inducible, constitutive expression of a transgenic protein or other molecule in a plant. A wide range of effective promoters, such as an embryo-specific promoter, permits the introduction of multiple transgenes into a plant; when each transgene is fused to a different promoter, the risk of DNA sequence homology dependent transgene inactivation (co-suppression) can be minimized.

An emb5 promoter sequence of the invention is exemplified by the nucleic acid sequence given in SEQ ID NO:1. Characterization of the nucleic acid sequence of SEQ ID NO:1 indicates that transcription initiation begins at about nucleotide 1553. Canonical TATA and CAAT boxes are identified as beginning at about nucleotides 1505 and 1411, respectively, in SEQ ID NO:1.

However, in addition to the unmodified emb5 promoter comprising a DNA molecule having the sequence of SEQ ID NO:1, the current invention includes derivatives of this DNA sequence and compositions made therefrom. One important application of the emb5 promoter will be in the construction of vectors designed for introduction into plants by genetic transformation.

3. Derivative emb5 Promoters

This invention provides derivatives of the embryo-specific promoter which has been derived from the 5' regulatory region of the maize emb5 gene. Derivatives of this promoter may include, but are not limited to, deletions of sequence, single or multiple point mutations, alterations at a particular restriction enzyme site, addition of functional elements, or other means of molecular modification which may enhance, or otherwise alter promoter expression. For example, one of skill in the art may delimit the functional elements within the emb5 promoter and delete any non-essential elements. Functional elements may be modified or combined to increase the utility or expression of the sequences of the invention for any particular application. For example, a functional region within the emb5 promoter of this invention can be modified to decrease or increase inducible expression. The means for mutagenizing or creating deletions in a DNA segment encoding any promoter sequence, such as an emb5 promoter sequence of the current invention, are well known to those of skill in the art and are disclosed, for example, in U.S. Pat. No. 6,583,338, incorporated herein by reference in its entirety.

It is anticipated that fragments of the emb5 promoter that are especially useful for allowing functionality include, but are not limited to, the about 100 nucleotide base pair 5' UTR region from the transcriptional start site to the ATG (about nucleotide 1553 to 1658 of SEQ ID NO:1), the about 250 nucleotide base pair 5' UTR region from the CAAT box to the ATG, including the TATA box (about nucleotide 1411 to about 1658 of SEQ ID NO:1), the about 140 nucleotide base pair 5' UTR region from the CAAT box to the transcriptional start site (from about nucleotide 1411 to about 1553 of SEQ ID NO:1), and the about 1000 or more nucleotide base pair 5' UTR region upstream of the CAAT box (from about nucleotide 1 to about 1411 of SEQ ID NO:1), and fragments thereof. The various fragments described may be operably joined to a heterologous DNA and used for plant transformation. Exogenous DNA comprising a marker gene or reporter gene is useful for testing the promoter activity of the various fragments. It is also anticipated that the sequences and fragments thereof upstream of the CAAT box (from about nucleotide 1 to about 1411 of SEQ ID NO:1) may be operably linked to heterologous CAAT and TATA boxes or other transcriptional start site sequences and exhibit promoter activity similar or identical to that of the maize emb5 promoter.

Thus, promoters of this invention are not required to have 100% sequence identity to SEQ ID NO:1. For instance, effective promoters can range from about 85% to about 100% identity to SEQ ID NO:1 or a fragment of SEQ ID NO:1, e.g. a DNA fragment of at least about 100 nucleotide base pairs, or larger, e.g., about 150, about 250 or about 100 nucleotide base pairs. In one aspect of the invention the promoters and derivative promoters are characterized as having at least about 85% sequence identity, more preferably at least about 90% sequence identity or higher, e.g., at least about 95% or even about 98% sequence identity with SEQ ID NO:1, or such a fragment thereof.

Promoters of this invention can also be derived from homologous genes from species other than maize. For example, promoters of this invention can be derived from the 5' regulatory region of a rice or wheat gene homologous to the maize emb5 gene.

4. Plant Transformation Constructs

The construction of vectors which may be employed in conjunction with plant transformation techniques according to the invention are known to those of skill of the art in light of the present disclosure. Many approaches or methods have been developed and used for gene cloning. Examples of these are cloning by restriction enzyme digestion and ligation of compatible ends, T-A cloning directly from PCR product, TOPO-attached unidirectional cloning, and recombination-based cloning.

Recombination-based cloning is one of the most versatile cloning methods available due to its high cloning efficiency and its broad application for cloning a variety of genes regardless of available restriction enzyme sites. Recombination cloning uses the lambda recombination system to clone genes into vectors that contain recombination sequences for the lambda recombinase machinery. Recombination cloning uses site-specific recombinases, which along with associated proteins in some cases, recognize specific sequences of bases in a nucleic acid molecule and exchange the nucleic acid segments flanking those sequences. The recombinases and associated proteins are collectively referred to as "recombination proteins." Site-specific recombinases are proteins that are present in many organisms (e.g., viruses and bacteria) and have been characterized as having both endonuclease and ligase properties.

Many of the known site-specific recombinases belong to the integrase family of recombinases including the Integrase/att system from bacteriophage lambda. An example of one application of the Integrase/att system from bacteriophage lambda is the LR cloning reaction as disclosed in U.S. Pat. Nos. 5,888,732 and 6,277,608 B1 and U.S. published patent application 2002/0007051 A1 and International application WO 02/081711 A1, all of which are incorporated herein by reference. The LR cloning reaction is commercially available as the GATEWAY™ cloning technology (available from Invitrogen Corporation, Carlsbad, Calif.). The LR cloning reaction is catalyzed by the LR Clonase Enzyme mix, which comprises lambda recombination proteins Int, Xis, and the *E. coli*-encoded protein IHF.

The techniques of the current invention are thus not limited to any particular DNA sequences in conjunction with the emb5 promoter of the invention. For example, the emb5 promoter alone could be transformed into a plant with the goal of enhancing or altering the expression of one or more genes in the host genome, particularly in the embryonic tissue. Useful exogenous DNA sequences to operably link to the promoter sequences of the invention are exemplified by sequence encoding proteins, polypeptide products, RNA molecules such as antisense RNA molecules, marker genes, or combinations thereof. In certain embodiments, the present inventors contemplate the transformation of a recipient cell with more than one transformation construct, a co-transformation. Preferred components likely to be included with vectors used in the current invention are as follows: regulatory elements including 3' untranslated regions, 5' untranslated regions, enhancers, introns, signal peptide coding sequences, transit peptide coding sequences, selectable marker genes, screenable marker genes, and the like.

A discussion of useful plant transformation constructs which can be prepared by those of ordinary skill in the art can be found among, for example, U.S. Pat. No. 5,641,876 which discloses a rice actin promoter, U.S. Pat. No. 6,429,357 which discloses a rice actin 2 promoter and intron, U.S. Patent Number Application Publication 2002/0192813A1 which discloses 5', 3' and intron elements useful in the design of effective plant expression vectors, and U.S. patent application Ser. No. 09/757,089 which discloses a maize chloroplast aldolase promoter, all of which are incorporated herein by reference.

In certain embodiments of the invention, transformation of a recipient cell may be carried out with more than one exogenous DNA. The DNA molecules may code for a protein product, or a non-protein product, such as a transfer RNA or anti-sense RNA. Two or more exogenous coding sequences can be supplied in a single transformation event using either distinct heterologous DNA vectors, or using a single vector incorporating two or more heterologous DNA sequences.

5. Exogenous Genes for Modification of Plant Phenotypes

The present invention provides methods and compositions for the efficient expression of selected DNA sequences in plant cells. In particular, the current invention provides an emb5 promoter for the expression of exogenous DNA in plants. Useful genes for expression during kernel development are genes which promote aspects of enhanced grain agronomic characteristics, grain fill, decreased kernel abortion, increased transport of nutrients and the like.

The choice of an exogenous DNA for expression in a plant host cell in accordance with the invention will depend on the purpose of the transformation. One of the major purposes of transformation of crop plants is to add commercially desirable, agronomically important or end-product traits to the plant. Such traits include, but are not limited to, herbicide resistance, herbicide tolerance, insect resistance, insect tolerance, disease resistance, disease tolerance (viral, bacterial, fungal, nematode), stress tolerance, stress resistance, as exemplified by resistance or tolerance to drought, heat, chilling, freezing, excessive moisture, salt stress and oxidative stress, increased yield, food content and value, increased feed content and value, physical appearance, male sterility, female sterility, drydown, standability, prolificacy, starch quantity and quality, oil quantity and quality, protein quality and quantity, amino acid composition, and the like. It is also anticipated that expression of exogenous DNA encoding antisense RNAs or other RNA molecules are included as useful means for modifying plant phenotype.

Useful nucleic acid sequences that can be combined with the promoter nucleic acid sequence of the present invention and provide improved end-product traits include, without limitation, those encoding seed storage proteins, fatty acid pathway enzymes, tocopherol biosynthetic enzymes, amino acid biosynthetic enzymes, and starch branching enzymes. A discussion of exemplary heterologous DNAs useful for the modification of plant phenotypes may be found in, for example, U.S. Pat. Nos. 6,194,636; 6,207,879; 6,232,526; 6,426,446; 6,429,357; 6,433,252, 6,437,217, 6,515,201 and 6,583,338 and PCT Publication WO 02/057471, each of which is specifically incorporated herein by reference in its entirety.

Preferred seed storage proteins include zeins (U.S. Pat. Nos. 4,886,878, 4,885,357, 5,215,912, 5,589,616, 5,508,468, 5,939,599, 5,633,436, and 5,990,384; PCT Publications WO 90/01869, WO 91/13993, WO 92/14822, WO 93/08682, WO 94/20628, WO 97/28247, WO 98/26064, and WO 99/40209), 7S proteins (U.S. Pat. Nos. 5,003,045, and 5,576,203), brazil nut protein (U.S. Pat. No. 5,850,024), phenylalanine free proteins (PCT Publication WO 96/17064), albumin (PCT Publication WO 97/35023), b-conglycinin (PCT Publication WO 00/19839), 11S (U.S. Pat. No. 6,107,051), alpha-hordothionin (U.S. Pat. Nos. 5,885,802, and 5,88,5801) arcelin seed storage proteins (U.S. Pat. No. 5,270,200) lectins (U.S. Pat. No. 6,110,891) and glutenin (U.S. Pat. Nos. 5,990,389, and 5,914,450) all of which are incorporated herein by reference.

Preferred fatty acid pathway enzymes include thioesterases (U.S. Pat. Nos. 5,512,482, 5,530,186, 5,945,585, 5,639,790, 5,807,893, 5,955,650, 5,955,329, 5,759,829, 5,147,792, 5,304,481, 5,298,421, 5,344,771, and 5,760,206), and desaturases (U.S. Pat. Nos. 5,689,050, 5,663,068, 5,614,393, 5,856,157, 6,117,677, 6,043,411, 6,194,167, 5,705,391, 5,663,068, 5,552,306, 6,075,183, 6,051,754, 5,689,050, 5,789,220, 5,057,419, 5,654,402, 5,659,645, 6,100,091, 5,760,206, 6,172,106, 5,952,544, 5,866,789, 5,443,974, and 5,093,249) all of which are incorporated herein by reference.

Preferred tocopherol biosynthetic enzymes include tyrA, slr1736, ATPT2, dxs, dxr, GGPPS, HPPD, GMT, MT1, tMT2, AANT1, slr 1737, and an antisense construct for homogentisic acid dioxygenase (Kridl et al., *Seed Sci. Res.* 1:209:219 (1991); Keegstra, *Cell* 56(2):247–53 (1989); Nawrath et al., *Proc. Natl. Acad. Sci. U.S.A.* 91:12760–12764 (1994); Xia et al., *J. Gen. Microbiol.* 138:1309–1316 (1992); Lois et al., *Proc. Natl. Acad. Sci. U.S.A.* 95 (5):2105–2110 (1998); Takahashi et al. *Proc. Natl. Acad. Sci. U.S.A.* 95 (17), 9879–9884 (1998); Norris et al., *Plant Physiol.* 117:1317–1323 (1998); Bartley and Scolnik, *Plant Physiol.* 104:1469–1470 (1994); Smith et al., *Plant J.* 11: 83–92 (1997); WO 00/32757; WO 00/10380; Saint Guily et al., *Plant Physiol.*, 100(2):1069–1071 (1992); Sato et al., *J. DNA Res.*7 (1):31–63 (2000)) all of which are incorporated herein by reference.

Preferred amino acid biosynthetic enzymes include anthranilate synthase (U.S. Pat. No. 5,965,727, PCT Publications WO 97/26366, WO 99/11800, and WO 99/49058), tryptophan decarboxylase (PCT Publication WO 99/06581), threonine decarboxylase (U.S. Pat. Nos. 5,534,421, and 5,942,660; PCT Publication WO 95/19442), threonine deaminase (PCT Publications WO 99/02656 and WO 98/55601), dihydrodipicolinic acid synthase (U.S. Pat. No. 5,258,300), diacylglycerol acyltransferase (U.S. Patent Publications 20030115632A1 and 20030028923A1), and aspartate kinase (U.S. Pat. Nos. 5,367,110, 5,858,749, and 6,040,160) all of which are incorporated herein by reference.

Preferred starch branching enzymes include those set forth in U.S. Pat. Nos. 6,232,122 and 6,147,279 and PCT Publication WO 97/22703, all of which are incorporated herein by reference.

Alternatively, an exogenous DNA sequence may be designed to down-regulate a specific nucleic acid sequence. This is typically accomplished by operably linking with a promoter, such as an emb5 promoter of the invention, an exogenous DNA in an antisense orientation or a DNA designed such that a hairpin-forming RNA molecule is generated upon transcription. Gene suppression may be effective against a native plant gene associated with a trait, e.g. to provide plants with reduced levels of a protein encoded by the native gene or with enhanced or reduced levels of an affected metabolite. For example, an emb5 promoter of the invention may be operably linked to a heterologous DNA designed such that a hairpin-shaped RNA is formed for suppression of a native gene in maize embryos.

As used herein "gene suppression" means any of the well-known methods for suppressing an RNA transcript or production of protein translated from an RNA transcript, including post-transcriptional gene suppression and transcriptional suppression. Post-transcriptional gene suppression is mediated by double-stranded RNA having homology to a gene targeted for suppression. Gene suppression by RNA transcribed from an exogenous DNA construct comprising an inverted repeat of at least part of a transcription unit is a common feature of gene suppression methods known as anti-sense suppression, co-suppression and RNA interference. Transcriptional suppression can be mediated by a transcribed double-stranded RNA having homology to promoter DNA sequence to effect what is called promoter trans-suppression.

More particularly, post transcriptional gene suppression by inserting an exogenous DNA construct with anti-sense oriented DNA to regulate gene expression in plant cells is disclosed in U.S. Pat. Nos. 5,107,065 and 5,759,829, each of which is incorporated herein by reference in its entirety. Transgenic plants transformed using such anti-sense oriented DNA constructs for gene suppression can comprise DNA arranged as an inverted repeat, as disclosed by Redenbaugh et al. in "Safety Assessment of Genetically Engineered Flavr Savr™ Tomato, CRC Press, Inc. (1992). Inverted repeat insertions can comprises a part or all of a T-DNA construct, e.g. an inverted repeat of transcription terminator sequence.

Post transcriptional gene suppression by inserting an exogenous DNA construct with sense-oriented DNA to regulate gene expression in plants is disclosed in U.S. Pat. Nos. 5,283,184 and 5,231,020, each of which is incorporated herein by reference.

Different types of exogenous DNA arrangements resulting in gene suppression are known to those of skill in the art and include but are not limited to the following. International Publication WO 94/01550 discloses DNA constructs where the anti-sense RNA was stabilized with a self-complementary 3' segment. Other double-stranded hairpin-forming elements in transcribed RNA are disclosed in International Publication No. 98/05770 where the anti-sense RNA is stabilized by hairpin forming repeats of poly(CG) nucleotides and Patent Application Publication No. 2002/0048814 A1 describes sense or anti-sense RNA stabilized by a poly(T)-poly(A) tail. U.S. Patent Application Publication No. 2003/0018993 A1 disclose sense or anti-sense RNA is stabilized by an inverted repeat of a subsequence of 3' untranslated region of the NOS gene. U.S. Patent Application Publication No. 2003/0036197 A1 describe an RNA stabilized by two complementary RNA regions having homology to a target sequence.

Gene silencing can also be effected by transcribing RNA from both a sense and an anti-sense oriented DNA, e.g. as disclosed in U.S. Pat. No. 5,107,065 and other examples as follows. U.S. Pat. No. 6,326,193 discloses gene targeted DNA which is operably linked to opposing promoters. Sijen et al., (The Plant Cell, Vol. 8, 2277–2294 (1996)) disclose the use of constructs carrying inverted repeats of a cowpea mosaic virus gene in transgenic plants to mediate virus resistance. Such constructs for post transcriptional gene suppression in plants by double-stranded RNA are also disclosed in International Publication No. WO 99/53050, International Publication No. WO 99/49029, U.S. Patent Application Publication No. 2003/0175965 A1, U.S. patent application Ser. No.10/465,800 and U.S. Pat. No. 6,506,559. See also U.S. application Ser. No. 10/393,347 which discloses constructs and methods for simultaneously expressing one or more recombinant genes while simultaneously suppressing one or more native genes in a transgenic plant. See also U.S. Pat. No. 6,448,473 which discloses multigene suppression vectors for use in plants. All of the above-described patents, applications and international publications disclosing materials and methods for post transcriptional gene suppression in plants are incorporated herein by reference.

Transcriptional suppression such as promoter trans suppression can be effected by a expressing a DNA construct comprising a promoter operably linked to inverted repeats of promoter DNA for a target gene. Constructs useful for such gene suppression mediated by promoter trans suppression are disclosed by Mette et al., (The EMBO Journal, Vol. 18, No. 1, pp. 241–148, 1999) and by Mette et al., (The EMBO Journal, Vol. 19, No. 19, pp. 5194–5201–148, 2000), both of which are incorporated herein by reference.

Preferable target nucleic acid sequences encode proteins which contain a low content of essential amino acids, yet are expressed at relatively high levels in particular tissues. For example, b-conglycinin and glycinin are expressed abundantly in seeds, but are nutritionally deficient with respect to essential amino acids. This antisense approach may also be used to effectively decrease the level of other undesirable proteins, such as antifeedants (e.g., lectins), albumin, and allergens, from plant-derived foodstuffs, or to down-regulate catabolic enzymes involved in degradation of desired compounds such as essential amino acids.

Any of the plants or parts thereof of the present invention may be processed to produce a feed, meal, protein or oil preparation. A particularly preferred plant part for this purpose is a seed. In a preferred embodiment the feed, meal, protein or oil preparation is designed for ruminant animals. Methods to produce feed, meal, protein and oil preparations are known in the art. See, for example, U.S. Pat. Nos. 4,957,748, 5,100,679, 5,219,596, 5,936,069, 6,005,076, 6,146,669, and 6,156,227. In a preferred embodiment, the protein preparation is a high protein preparation. Such a high protein preparation preferably has a protein content of greater than 5% w/v, more preferably 10% w/v, and even more preferably 15% w/v.

In a preferred oil preparation, the oil preparation is a high oil preparation with an oil content derived from a plant or part thereof of the present invention of greater than about 5% w/v, more preferably greater than about 10% w/v, and even more preferably greater than about 15% w/v. In a preferred embodiment the oil preparation is a liquid and of a volume greater than about 1, about 5, about 10 or about 50 liters. The present invention provides for oil produced from plants of the present invention or generated by a method of the present invention. Such oil may be a minor or major component of any resultant product. Moreover, such oil may be blended with other oils. In a preferred embodiment, the oil produced from plants of the present invention or generated by a method of the present invention constitutes greater than about 0.5%, about 1%, about 5%, about 10%, about 25%, about 50%, about 75% or about 90% by volume or weight of the oil component of any product. In another embodiment, the oil preparation may be blended and can constitute greater than about 10%, about 25%, about 35%, about 50% or about 75% of the blend by volume. Oil produced from a plant of the present invention can be admixed with one or more organic solvents or petroleum distillates.

In a further embodiment, meal of the present invention may be blended with other meals. In a preferred embodiment, the meal produced from plants of the present invention or generated by a method of the present invention constitutes greater than about 0.5%, about 1%, about 5%, about 10%, about 25%, about 50%, about 75% or about 90% by volume or weight of the meal component of any product. In another embodiment, the meal preparation may be blended and can constitute greater than about 10%, about 25%, about 35%, about 50% or about 75% of the blend by volume.

6. Assays of Transgene Expression

To confirm the presence of an exogenous DNA in regenerated plants, a variety of assays may be performed. Such assays include, for example, molecular biological assays such as Southern and Northern blotting and PCR; biochemical assays such as detecting the presence of a protein product, e.g., by immunological means (ELISAs and Western blots) or by enzymatic function; plant part assays such as leaf or root assays; and in some cases phenotype analysis of a whole regenerated plant. Additional assays useful for determining the efficiency of transgene expression and promoter function also include without limitation fluorescent in situ hybridization (FISH), direct DNA sequencing, pulsed field gel electrophoresis (PFGE) analysis, single-stranded conformation analysis (SSCA), RNase protection assay, allele-specific oligonucleotide (ASO), dot blot analysis, denaturing gradient gel electrophoresis, RT-PCR, quantitative RT-PCR, RFLP and PCR-SSCP. Such assays are known to those of skill in the art.

7. Methods for Plant Transformation

Suitable methods for plant transformation for use with the current invention are believed to include virtually any method by which DNA can be introduced into a cell, such as by direct delivery of DNA such as by PEG-mediated transformation of protoplasts, by electroporation, by agitation with silicon carbide fibers, by Agrobacterium-mediated transformation and by acceleration of DNA coated particles, etc. Through the application of techniques such as these, maize cells, as well as those of virtually any other plant species, may be stably transformed, and these cells developed into transgenic plants. In certain embodiments, acceleration methods are preferred and include, for example, microprojectile bombardment and the like. Preferred methods of plant transformation are microprojectile bombardment as illustrated in U.S. Pat. Nos. 5,015,580; 5,550,318; 5,538,880; 6,160,208; 6,399,861 and 6,403,865 and Agrobacterium-mediated transformation as illustrated in U.S. Pat. Nos. 5,635,055; 5,824,877; 5,591,616; 5,981,840 and 6,384,301, all of which are incorporated herein by reference.

The seeds of this invention can be harvested from fertile transgenic plants and be used to grow progeny generations of transformed plants of this invention including hybrid plants line comprising the DNA construct operably linked to the emb5 promoter.

8. Recipient Cells for Transformation

Transformation methods of this invention to provide plants comprising an exogenous DNA operably linked to the emb5 promoter are preferably practiced in tissue culture on media and in a controlled environment. "Media" refers to the numerous nutrient mixtures that are used to grow cells in vitro, that is, outside of the intact living organism. The medium usually is a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. Rate of cell growth also will vary among cultures initiated with the array of media that permit growth of that cell type.

Recipient cell targets include, but are not limited to, meristem cells, callus, immature embryos and gametic cells such as microspores, pollen, sperm and egg cells. It is contemplated that any cell from which a fertile plant may be regenerated is useful as a recipient cell. Callus may be initiated from tissue sources including, but not limited to, immature embryos, seedling apical meristems, microspores and the like. Those cells which are capable of proliferating as callus also are recipient cells for genetic transformation. The present invention provides techniques for transforming immature embryos and subsequent regeneration of fertile transgenic plants. Practical transformation methods and materials for making transgenic plants of this invention, e.g. various media and recipient target cells, transformation of immature embryos and subsequent regeneration of fertile transgenic plants are disclosed in U.S. Pat. No. 6,194,636 and U.S. patent application Ser. No. 09/757,089, which are incorporated herein by reference.

9. Production and Characterization of Stably Transformed Plants

After effecting delivery of exogenous DNA to recipient cells, the next steps generally concern identifying the transformed cells for further culturing and plant regeneration. As mentioned herein, in order to improve the ability to identify transformants, one may desire to employ a selectable or screenable marker gene as, or in addition to, the expressible gene of interest. In this case, one would then generally assay the potentially transformed cell population by exposing the cells to a selective agent or agents, or one would screen the cells for the desired marker gene trait.

It is believed that DNA is introduced into only a small percentage of target cells in any one experiment. In order to provide an efficient system for identification of those cells receiving DNA and integrating it into their genomes one may employ a means for selecting those cells that are stably transformed. One exemplary embodiment of such a method is to introduce into the host cell, a marker gene which confers resistance to some normally inhibitory agent, such as an antibiotic or herbicide. Examples of antibiotics which may be used include those conferring resistance to antibiotics such as kanamycin (nptII), hygromycin B (aph IV) and gentamycin (aac3 and aacC4) or resistance to herbicides such as glufosinate (bar or pat) and glyphosate (EPSPS). Examples of such selectable are illustrated in U.S. Pat. Nos. 5,550,318; 5,633,435; 5,780,708 and 6,118,047, all of which are incorporated herein by reference.

Cells that survive the exposure to the selective agent, or cells that have been scored positive in a screening assay, may be cultured in media that supports regeneration of plants. Ideally, seed from the transgenic plant is collected. Screenable markers which provide an ability to visually identify transformants can also be employed, e.g., a gene expressing a colored or fluorescent protein such as a luciferase or green fluorescent protein (GFP) or a gene expressing a beta-glucuronidase or uidA gene (GUS) for which various chromogenic substrates are known.

10. Site Specific Integration or Excision of Transgenes

It is specifically contemplated by the inventors that one could employ techniques for the site-specific integration or excision of transformation constructs prepared in accordance with the instant invention. An advantage of site-specific integration or excision is that it can be used to overcome problems associated with conventional transformation techniques, in which transformation constructs typically randomly integrate into a host genome and multiple copies of a construct may integrate. This random insertion of introduced DNA into the genome of host cells can be detrimental to the cell if the exogenous DNA inserts into an essential gene. In addition, the expression of a transgene may be influenced by "position effects" caused by the surrounding genomic DNA. Further, because of difficulties associated with plants possessing multiple transgene copies, including gene silencing, recombination and unpredictable inheritance, it is typically desirable to control the copy number of the inserted DNA, often only desiring the insertion of a single copy of the DNA sequence.

Site-specific integration can be achieved in plants by means of homologous recombination DNA can be inserted into the host genome by a homologous recombination reaction involving either a single reciprocal recombination (resulting in the insertion of the entire length of the introduced DNA) or through a double reciprocal recombination (resulting in the insertion of only the DNA located between the two recombination events).

A number of different site specific recombinase systems can be employed in accordance with the instant invention, including, but not limited to, the Cre/lox system of bacteriophage P1, the FLP/FRT system of yeast, the Gin recombinase of phage Mu, the Pin recombinase of *E. coli*, and the R/RS system of the pSR1 vector. The bacteriophage P1 Cre/lox and the yeast FLP/FRT systems constitute two particularly useful systems for site specific integration or excision of transgenes. In these systems, a recombinase (Cre or FLP) will interact specifically with its respective site-specific recombination sequence (lox or FRT, respectively) to invert or excise the intervening sequences. The sequence for each of these two systems is relatively short (34 bp for lox and 47 bp for FRT) and therefore, convenient for use with transformation vectors. The FLP/FRT and Cre/lox recombinase systems have been demonstrated to function efficiently in plant cells. A more thorough discussion of site-specific integration or excision of transgenes may be found, for example, in U.S. Pat. Nos. 4,959,317 and 5,527, 695, both of which are incorporated herein by reference in their entirety.

11. Deletion of Sequences Located within the Transgenic Insert

During the transformation process, it is often necessary to include ancillary sequences, such as selectable marker or reporter genes, for tracking the presence or absence of a desired trait gene transformed into the plant on the DNA construct. Such ancillary sequences often do not contribute to the desired trait or characteristic conferred by the phenotypic trait gene. Homologous recombination is a method by which introduced sequences may be selectively deleted in transgenic plants.

Deletion of sequences by homologous recombination relies upon directly repeated DNA sequences positioned about the region to be excised in which the repeated DNA sequences direct excision utilizing native cellular recombination mechanisms. The first fertile transgenic plants are crossed to produce either hybrid or inbred progeny plants, and from those progeny plants, one or more second fertile transgenic plants are selected which contain a second DNA sequence that has been altered by recombination, preferably resulting in the deletion of the ancillary sequence. The first fertile plant can be either hemizygous or homozygous for the DNA sequence containing the directly repeated DNA which will drive the recombination event.

The directly repeated sequences are located 5' and 3' to the target sequence in the transgene. As a result of the recombination event, the transgene target sequence may be deleted, amplified or otherwise modified within the plant genome. In a preferred embodiment, a deletion of the target sequence flanked by the directly repeated sequence will result. See U.S. Pat. No. 6,580,019, incorporated herein by reference in its entirety, for additional discussion of the deletion of sequences located within a transgenic insert.

12. Breeding Plants of the Invention

This invention contemplates both plants directly regenerated from cells which have been transformed with a DNA construct of this invention as well as progeny of such plants, e.g. inbred progeny and hybrid progeny of transformed plants. This invention contemplates transgenic plants produced by direct transformation with a DNA construct of this invention and transgenic plants made by crossing a plant having a construct of the invention to a second plant lacking the construct. Crossing can comprise the following steps:
(a) plant seeds of the first parent plant (e.g. non-transgenic or a transgenic) and a second parent plant having a transgenic DNA construct;
(b) grow the seeds of the first and second parent plants into plants that bear flowers;
(c) pollinate a flower from the first parent plant with pollen from the second parent plant; and
(d) harvest seeds produced on the parent plant bearing the fertilized flower.

It is often desirable to introgress transgenes into elite varieties, e.g. by backcrossing, to transfer a specific desirable trait from one source to an inbred or other plant that lacks that trait. This can be accomplished, for example, by first crossing a superior inbred (A) (recurrent parent) to a donor inbred (non-recurrent parent), which carries the appropriate gene(s) for the trait in question, for example, a construct prepared in accordance with the current invention. The progeny of this cross first are selected in the resultant progeny for the desired trait to be transferred from the non-recurrent parent, then the selected progeny are mated back to the superior recurrent parent (A). After five or more backcross generations with selection for the desired trait, the progeny are hemizygous for loci controlling the characteristic being transferred, but are like the superior parent for most or almost all other genes. The last backcross generation would be selfed to give progeny which are pure breeding for the gene(s) being transferred, i.e. one or more transformation events.

Therefore, through a series of breeding manipulations, a transgene may be moved from one line into an entirely different line without the need for further recombinant manipulation. Transgenes are valuable in that they typically behave genetically as any other gene and can be manipulated by breeding techniques in a manner identical to any other corn gene. Therefore, one may produce inbred plants which are true breeding for one or more transgenes. By crossing different inbred plants, one may produce a large number of different hybrids with different combinations of transgenes. In this way, plants may be produced which have the desirable agronomic properties frequently associated with hybrids ("hybrid vigor"), as well as the desirable characteristics imparted by one or more transgene(s).

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized. The usefulness of marker assisted selection in breeding transgenic plants of the current invention, as well as types of useful molecular markers, such as but not limited to SSRs and SNPs, are discussed in PCT Application WO/02062129 and U.S. patent application Ser. Nos. 2002133852, 20030049612, and 2003005491 each of which is incorporated herein by reference in their entirety.

The ultimate goal in plant transformation is to produce plants which are useful to people. In this respect, transgenic plants created in accordance with the current invention may be used for virtually any purpose deemed of value to the grower or to the consumer. For example, one may wish to harvest seed for planting purposes, or products may be made from the seed itself such as oil, starch, animal or human food, pharmaceuticals, and various industrial products. Maize is used extensively in the food and feed industries, as well as in industrial applications. Further discussion of the uses of maize can be found, for example, in U.S. Pat. Nos. 6,194,636; 6,207,879; 6,232,526; 6,426,446; 6,429,357; 6,433,252, 6,437,217 and 6,583,338 and PCT Publications WO 95/06128 and WO 02/057471, each of which is specifically incorporated herein by reference in its entirety.

13. Examples

The following examples are included to illustrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

EXAMPLE 1

This example discloses a method for cloning the maize emb5 promoter. The 5' regulatory region of a maize embryo-specific emb5 gene was isolated from genomic DNA of a public maize line Missouri 17 (MO17). Oligonucleotide primers of SEQ ID NO:2 and SEQ ID NO:3 for the PCR reaction were designed based upon a public protein sequence for maize emb5 (Williams and Tsang, *Plant Physiol.*, 100:1067–1068, 1992; MZEEMBIV; accession number M90554) and were used to PCR amplify the a portion of the emb5 promoter from MO17 genomic DNA. The cloned fragment was used as a probe against maize MO17 genomic DNA lambda FIX II from which a genomic clone containing additional emb5 promoter sequence was isolated. Addition PCR using PCR primers EMPRO-433 (SEQ ID NO:4) and EMPRO-1 (SEQ ID NO:5) and standard cloning procedures were used to clone the emb5 promoter having the sequence of SEQ ID NO:1 contained in a vector designated pEMpro.

EXAMPLE 2

Figure 1:
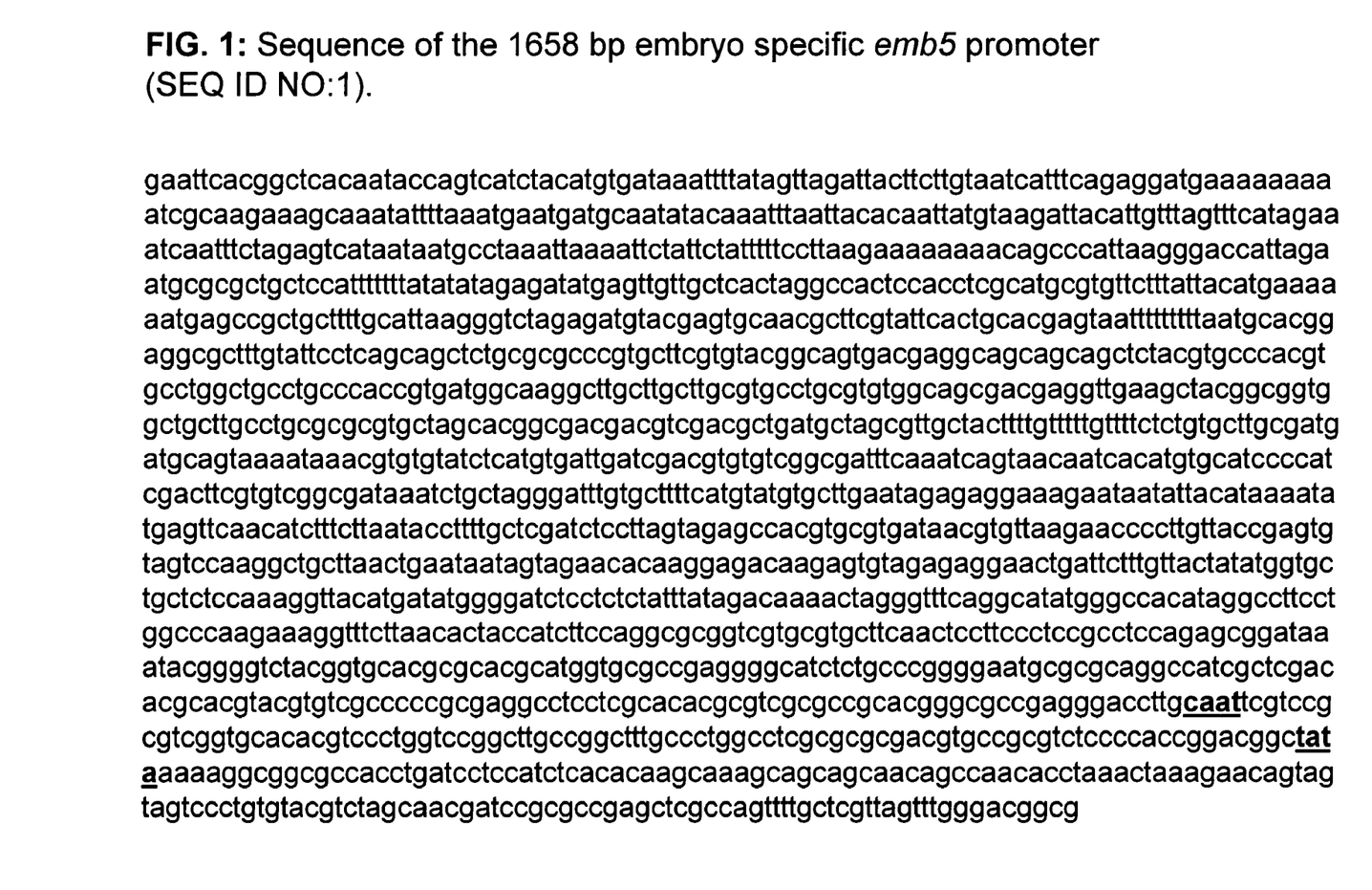
FIG. 1 is 1658 bp of DNA sequence comprising a maize embryo specific emb5 promoter element (SEQ ID NO:1).
Figure 2:
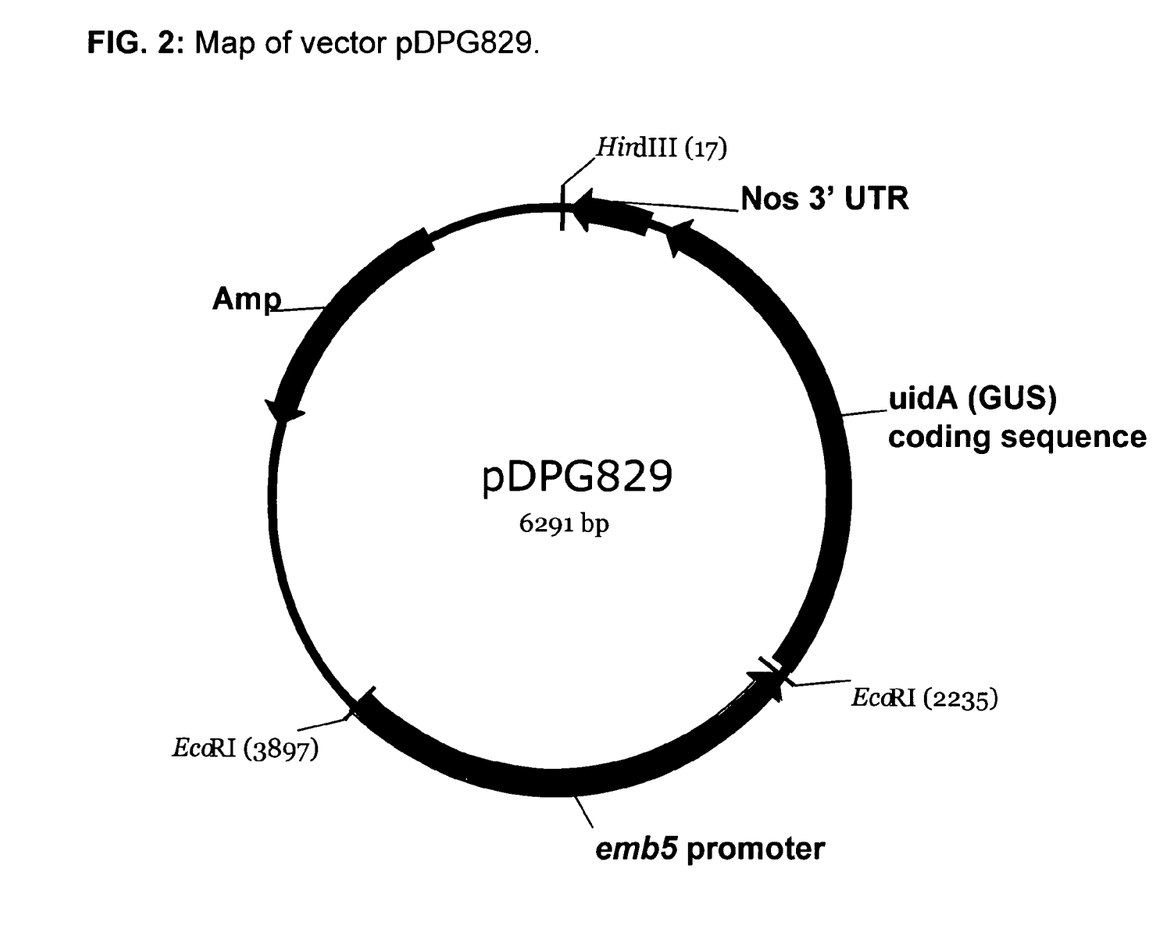
FIGS. 2, 3 and 4 illustrate maps of vectors pDPG829, pDPG830 and pMON67914, which contain a promoter of this invention.
Figure 3:
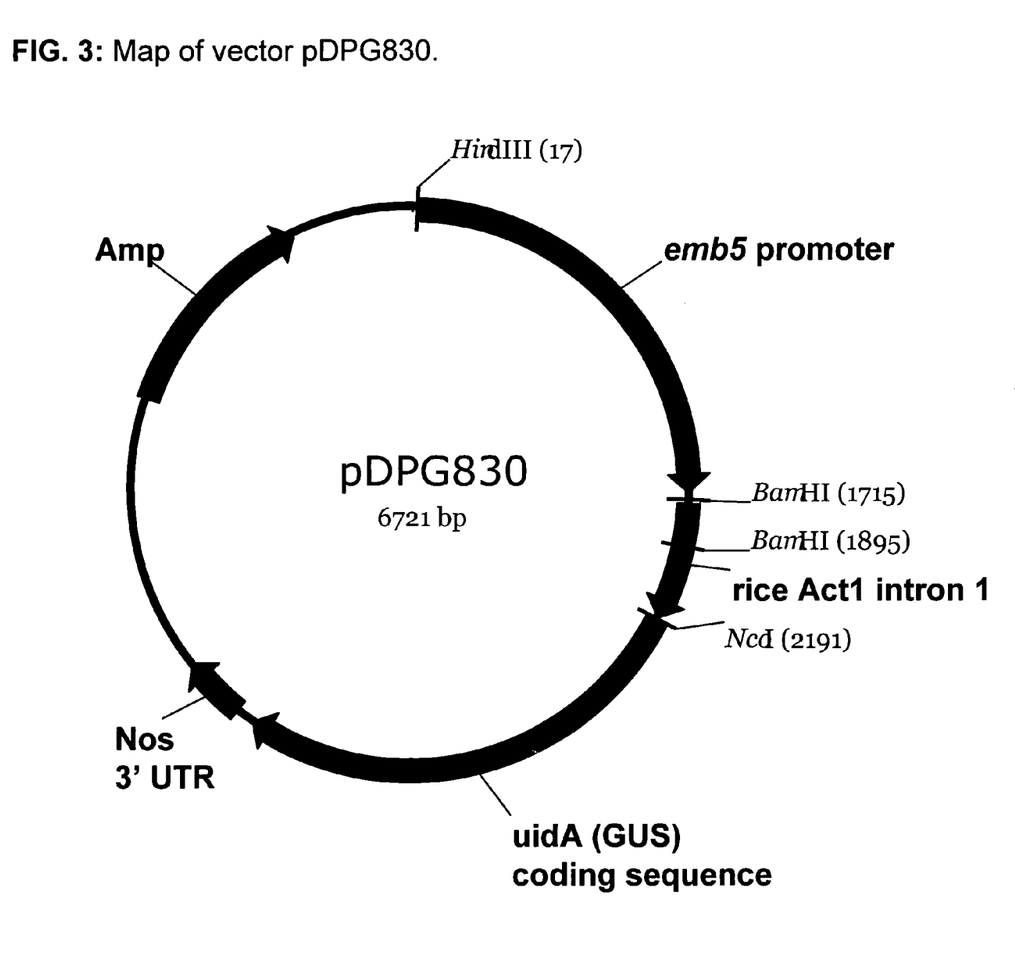
Figure 4:
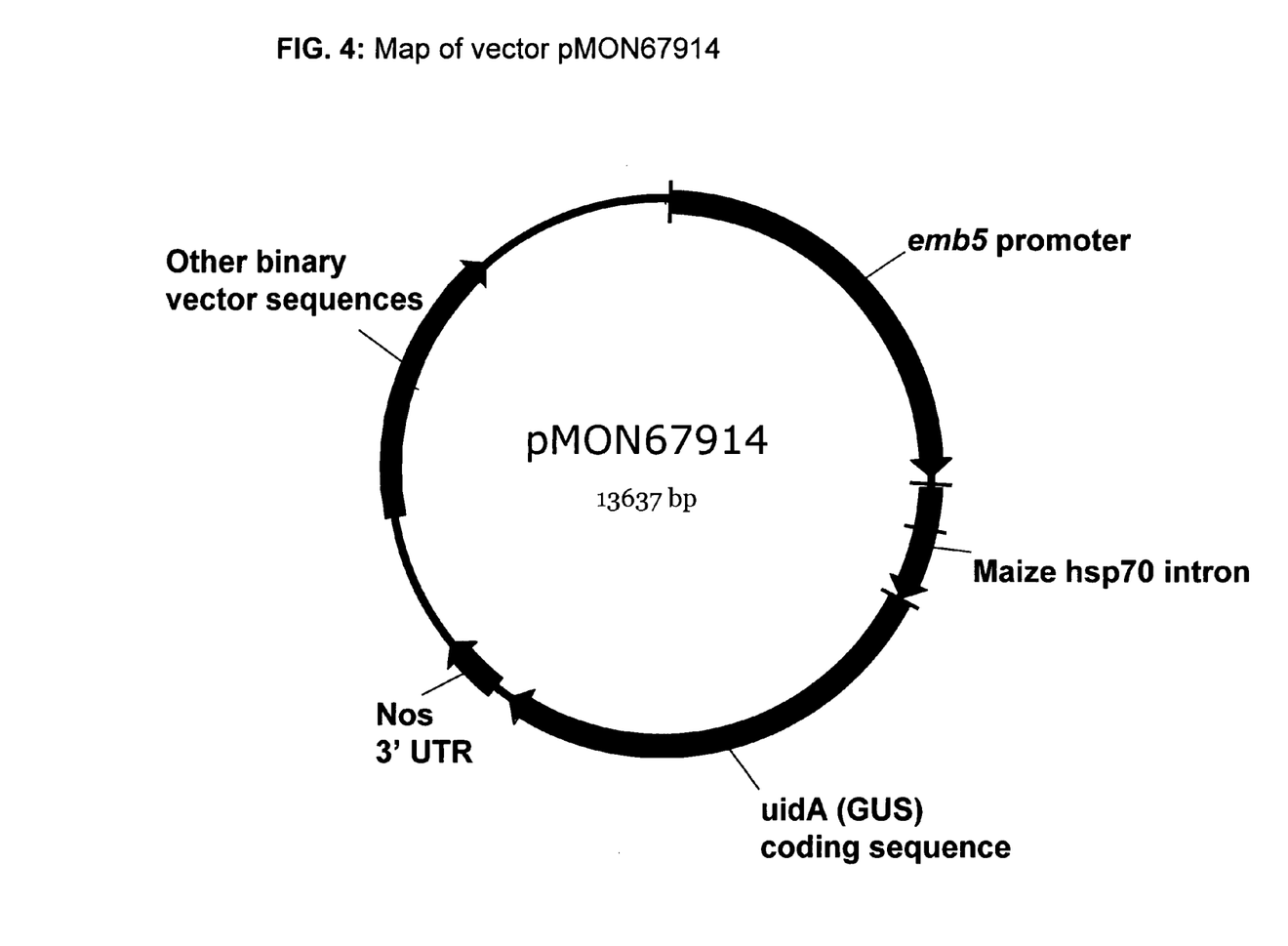

This example describes transformation vectors comprising a maize emb5 promoter operably linked to a uidA screenable marker gene (the protein product is commonly referred to as GUS). In each vector, the promoter had the sequence of SEQ ID NO:1. Vector pDPG829 (FIG. 2) comprised the emb5 promoter joined to the uidA screenable marker gene followed by a nos 3' UTR (from Agrobacterium). Vector pDPG830 (FIG. 3) comprised the emb5 promoter adjacent to the intron 1 from the rice actin 1 gene (U.S. Pat. No. 5,641,876) followed by the uidA screenable marker gene and a nos 3' UTR. Vector pMON67914 (FIG. 4) comprised the emb5 promoter adjacent to the maize hsp70 intron (U.S. Pat. No. 5,424,412) followed by the uidA screenable marker gene and a nos 3' UTR.

EXAMPLE 3

This example describes suitable transformation methods useful for introducing exogenous DNA constructs comprising a maize emb5 promoter into plant cells.

Biolistic transformation of maize was carried out with vectors pDPG829 and pDPG830 as described in Example 2. DNA coated microprojectiles were prepared with adherent DNA vectors pDPG829 or pDPG830 and the particles were bombarded into maize cells. *Agrobacterium tumefaciens*-mediated transformation of maize was carried out using vector pMON67914. The treated cells were then allowed to recover and regenerated on various media until they were of suitable condition for regeneration into plants, preferably fertile plants.

Fertile transgenic plants were produced from transformed maize cells. Regenerated $R_0$ and $R_1$ plants from a number of independent transformation events were assayed for GUS activity by histochemical staining, thus indicating the expression of the uidA reporter gene operably linked to an emb5 promoter of the invention.

EXAMPLE 4

This example describes the analysis of maize plants transformed to comprise a maize emb5 promoter. Analysis of maize emb5 promoter expression in fertile transgenic maize was determined. Regenerated plants from a number of independent transformation events were assayed for GUS activity by histochemical staining and were positive for uidA reporter gene expression as driven by the maize emb5 promoter (Tables 1 and 2). UidA reporter gene expression in the transgenic plants was assayed in the kernel and embryo at various times during the development.

In stably transformed $R_0$ maize plants produced from the transformation procedure using vectors pDPG829, pDPG830 and pMON67914, the maize emb5 promoter was shown to drive expression of GUS protein in the embryo of developing maize kernels (Table 1). The emb5 promoter alone (vector pDPG829) showed expression in the embryo of developing kernels at approximately 16 days after pollination (DAP). GUS expression was not observed in some samples at this same point in time for this construct. The emb5 promoter in conjunction with the rice actin 1 intron 1 (pDPG830) also resulted in GUS expression in the embryo. Expression levels were lowest in the embryo at 8 days after pollination, increased at 9 days after pollination and were observed to be highest at 20 days after pollination.

The emb5 promoter in combination with the maize hsp70 intron (pMON67914) showed GUS expression in the embryo at 21 DAP with an increased amount detected at 35 DAP (Table 2). Leaf, root, stem, cob and shank tissues of plants transformed with vector pMON67914 were sampled at 2 DAP did not exhibit GUS expression.

TABLE 1

GUS Expression in Maize Tissues as Driven by the Maize emb5 Promoter in pDPG829 or pDPG830.

| pDPG829 | Tissue | Expression | pDPG830 | Tissue | Expression |
|---|---|---|---|---|---|
| 8 DAP | kernel | 0 | 8 DAP | embryo | + |
| 9 DAP | NT | NT | 9 DAP | embryo | +++ |
| 10 DAP | NT | NT | 10 DAP | kernel | +++ |
| 16 DAP | embryo | +++ | 16 DAP | NT | NT |
| 20 DAP | NT | NT | 20 DAP | embryo | ++++ |

(+) is lowest expression level after overnight stain
(++++) is highest expression level after ~4 hr staining
(0) is no GUS expression detected after ~4 hr staining
NT is not tested

TABLE 2

GUS Expression in Maize Tissues as Driven
by the Maize emb5 Promoter in MON67914.

| PMON67914 | Tissue | Expression |
|---|---|---|
| 2 DAP | Embryo | 0 |
| 7 DAP | embryo | 0 |
| 14 DAP | embryo | 0 |
| 21 DAP | embryo | + |
| 35 DAP | embryo | ++ |

+ indicates expression
++ indicates expression to a greater level than +

EXAMPLE 5

This example illustrates the preparation and testing of derivatives of the emb5 promoter. A number of mutations, alteration or sub-fragments of the emb5 promoter are prepared and tested for promoter activity.

A progressive exonuclease enzyme, such as Bal31, is used to create a series of deletions of the emb5 promoter. The deletions are made from the 5' side, the 3' side, and from both the 5' and 3' ends. The fragments are operably linked to the uidA (GUS) gene followed by a 3' untranslated region. Other methods useful for making derivatives of the promoter of the instant invention include, but are not limited to, point mutations made in one or more nucleic acid residues, or digestion with restriction endonucleases followed by filling in or cleaving away overhangs followed by religation. Motifs may be identified and altered in the emb5 promoter in terms of size or number or orientation or sequence. Enhancer or intron sequences may also be useful for testing expression of the subfragments. Tissue at various stages of the transformation process, or young plantlets, fertile mature plants and kernel embryos is tested for gene expression. Fragments having effective promoter activity are identified by GUS analysis.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A transgenic plant having in its genome an exogenous DNA construct comprising a promoter operably linked to a heterologous DNA, wherein said promoter comprises the nucleotide sequence set forth in SEQ ID NO: 1 or at least 100 contiguous nucleotides from nucleotides 1–1553 of SEQ ID NO: 1 and exhibits embryo-specific promoter activity in plants.

2. A transgenic plant according to claim 1 wherein said promoter comprises DNA with a nucleic acid sequence of SEQ ID NO:1.

3. A transgenic plant according to claim 1 wherein said promoter comprises at least 100 contiguous nucleotides of SEQ ID NO:1.

4. A transgenic plant according to claim 1 wherein said promoter comprises CAAT and TATA box elements.

5. A transgenic plant according to claim 1 wherein said heterologous DNA encodes a molecule imparting at least one characteristic selected from the group consisting of insect resistance or tolerance; viral, bacterial, fungal, or nematode disease resistance or tolerance; herbicide resistance or tolerance; enhanced grain composition or quality; enhanced nutrient transporter functions; enhanced environmental stress tolerance; reduced mycotoxin contamination; a selectable marker phenotype; a screenable marker phenotype; a negative selectable marker phenotype; altered plant agronomic characteristics; enhanced kernel development; enhanced embryo development; enhanced grain agronomic characteristics; enhanced grain processing characteristics; and a combination thereof during embryo development.

6. A transgenic plant according to claim 1 wherein said heterologous DNA transcribes to RNA imparting gene suppression of at least one gene in said transgenic plant.

7. A transgenic plant according to claim 6 wherein said heterologous DNA transcribes to double-stranded RNA for suppressing a native gene in an embryo of said transgenic plant.

8. A transgenic plant according to claim 1 wherein expression of said heterologous DNA in a developing embryo in a seed of said transgenic plant increases the nutritional quality of said seed.

9. A transgenic plant according to claim 8 wherein said heterologous DNA encodes one or more proteins in the group consisting of dihydropicolinate synthase, aspartate kinase, anthranilate synthase, and diacylglycerol acyltransferase.

10. A transgenic plant according to claim 1 which is a corn, soybean, cotton, wheat, rice or canola plant.

11. Seed from a transgenic plant of claim 1, wherein said seed contains said exogenous DNA construct.

12. Seed from a transgenic plant of claim 10, wherein said seed contains said exogenous DNA construct.

13. Seed for producing a transgenic plant of claim 10, wherein said seed contains said exogenous DNA construct.

14. A DNA construct comprising an embryo-specific promoter comprising the nucleotide sequence set forth in SEQ ID NO: 1 or at least 100 contiguous nucleotides from nucleotides 1–1553 of SEQ ID NO: 1, wherein said promoter is operably linked to a heterologous DNA.

15. A DNA construct according to claim 14 wherein said promoter comprises DNA having the nucleic acid sequence of SEQ ID NO:1.

16. A DNA construct according to claim 14 wherein said promoter comprises at least 100 contiguous nucleotides from nucleotides 1–1553 of SEQ ID NO: 1.

17. A method for providing a transgenic plant which produces RNA of interest during embryo development comprising introducing into the genome of said plant a DNA construct according to claim 14.

18. An isolated DNA having embryo-specific promoter activity in plants and comprising at least 100 contiguous nucleotides from nucleotides 1–1553 of SEQ ID NO: 1.

* * * * *

SEQUENCE LISTING

```
<160> NUMBER OF SEQ ID NOS: 5

<210> SEQ ID NO 1
<211> LENGTH: 1658
<212> TYPE: DNA
<213> ORGANISM: Zea mays

<400> SEQUENCE: 1
gaattcacgg ctcacaatac cagtcatcta catgtgataa attttatagt tagattactt      60
cttgtaatca tttcagagga tgaaaaaaaa atcgcaagaa agcaaatatt ttaaatgaat     120
gatgcaatat acaaatttaa ttacacaatt atgtaagatt acattgttta gtttcataga     180
aatcaatttc tagagtcata ataatgccta aattaaaatt ctattctatt tttccttaag     240
aaaaaaaaca gcccattaag ggaccattag aatgcgcgct gctccatttt tttatatata     300
gagatatgag ttgttgctca ctaggccact ccacctcgca tgcgtgttct ttattacatg     360
aaaaaatgag ccgctgcttt tgcattaagg gtctagagat gtacgagtgc aacgcttcgt     420
attcactgca cgagtaattt tttttttaatg cacggaggcg ctttgtattc ctcagcagct     480
ctgcgcgccc gtgcttcgtg tacggcagtg acgaggcagc agcagctcta cgtgcccacg     540
tgcctggctg cctgcccacc gtgatggcaa ggcttgcttg cttgcgtgcc tgcgtgtggc     600
agcgacgagg ttgaagctac ggcggtggct gcttgcctgc gcgcgtgcta gcacggcgac     660
gacgtcgacg ctgatgctag cgttgctact tttgttttg ttttctctgt gcttgcgatg     720
atgcagtaaa ataaacgtgt gtatctcatg tgattgatcg acgtgtgtcg gcgatttcaa     780
atcagtaaca atcacatgtg catcccatc gacttcgtgt cggcgataaa tctgctaggg     840
atttgtgctt ttcatgtatg tgcttgaata gagaggaaag aataatatta cataaaatat     900
gagttcaaca tctttcttaa tacctttgc tcgatctcct tagtagagcc acgtgcgtga     960
```

-continued

```
taacgtgtta agaacccctt gttaccgagt gtagtccaag gctgcttaac tgaataatag    1020
tagaacacaa ggagacaaga gtgtagagag gaactgattc tttgttacta tatggtgctg    1080
ctctccaaag gttacatgat atggggatct cctctctatt tatagacaaa actagggttt    1140
caggcatatg ggccacatag gccttcctgg cccaagaaag gtttcttaac actaccatct    1200
tccaggcgcg gtcgtgcgtg cttcaactcc ttccctccgc ctccagagcg gataaatacg    1260
gggtctacgg tgcacgcgca cgcatggtgc gccgaggggc atctctgccc ggggaatgcg    1320
cgcaggccat cgctcgacac gcacgtacgt gtcgccccg cgaggcctcc tcgcacacgc     1380
gtcgcgccgc acgggcgccg agggaccttg caattcgtcc gcgtcggtgc acacgtccct    1440
ggtccggctt gccggctttg ccctggcctc gcgcgcgacg tgccgcgtct ccccaccgga    1500
cggctataaa aaggcggcgc cacctgatcc tccatctcac acaagcaaag cagcagcaac    1560
agccaacacc taaactaaag aacagtagta gtccctgtgt acgtctagca acgatccgcg    1620
ccgagctcgc cagttttgct cgttagtttg ggacggcg                            1658
```

<210> SEQ ID NO 2
<211> LENGTH: 20
<212> TYPE: DNA
<213> ORGANISM: Zea mays

<400> SEQUENCE: 2

```
ggtcaggaaa gcagggagga                                                  20
```

<210> SEQ ID NO 3
<211> LENGTH: 20
<212> TYPE: DNA
<213> ORGANISM: Zea mays

<400> SEQUENCE: 3

```
ggggcacgca tcagatctag                                                  20
```

<210> SEQ ID NO 4
<211> LENGTH: 21
<212> TYPE: DNA
<213> ORGANISM: Zea mays

<400> SEQUENCE: 4

```
actccttccc tccgcctcca g                                                21
```

<210> SEQ ID NO 5
<211> LENGTH: 21
<212> TYPE: DNA
<213> ORGANISM: Zea mays

<400> SEQUENCE: 5

```
cgccgtccca aactaacgag c                                                21
```